(12) United States Patent
Lewis et al.

(10) Patent No.: US 11,707,311 B2
(45) Date of Patent: Jul. 25, 2023

(54) BONE FASTENER AND DRIVER WITH RETAINING FEATURES

(71) Applicants: Adam Isaac Lewis, Madison, MS (US); Chase Thornburg, Cumming, GA (US)

(72) Inventors: Adam Isaac Lewis, Madison, MS (US); Chase Thornburg, Cumming, GA (US)

(*) Notice: Subject to any disclaimer, the term of this patent is extended or adjusted under 35 U.S.C. 154(b) by 264 days.

(21) Appl. No.: 17/165,297

(22) Filed: Feb. 2, 2021

(65) Prior Publication Data

US 2021/0236185 A1 Aug. 5, 2021

Related U.S. Application Data

(60) Provisional application No. 62/970,326, filed on Feb. 5, 2020.

(51) Int. Cl.
*A61B 17/88* (2006.01)
*A61B 17/86* (2006.01)

(52) U.S. Cl.
CPC ...... *A61B 17/8888* (2013.01); *A61B 17/8615* (2013.01)

(58) Field of Classification Search
CPC .............. A61B 17/888; A61B 17/8883; A61B 17/8888; A61B 17/8886; A61B 17/8891; A61B 17/7082; B25G 1/005; B25G 1/063; B25B 23/0057; B25B 23/101
See application file for complete search history.

(56) References Cited

U.S. PATENT DOCUMENTS

| | | | | |
|---|---|---|---|---|
| 203,581 A | * | 5/1878 | Birch | B25B 13/28 81/137 |
| 1,250,682 A | * | 12/1917 | Sholl | B25B 23/101 81/453 |
| 1,676,775 A | * | 7/1928 | Doherty | B25B 27/00 29/262 |
| 2,562,347 A | * | 7/1951 | Louise | B25B 23/106 81/444 |
| 2,634,641 A | | 4/1953 | Hodges | |
| 4,140,161 A | * | 2/1979 | Russo | B25B 23/10 81/451 |
| 5,484,440 A | | 1/1996 | Allard | |
| 5,605,080 A | | 2/1997 | Pfefferle et al. | |
| 5,885,299 A | * | 3/1999 | Winslow | A61B 17/861 606/247 |
| 6,189,422 B1 | * | 2/2001 | Stihl | B25B 15/02 81/452 |
| 6,382,977 B1 | | 5/2002 | Kumar | |

(Continued)

*Primary Examiner* — David W Bates
(74) *Attorney, Agent, or Firm* — David L. King

(57) ABSTRACT

A bone fastener driver assembly with a bone fastener retention feature has an outer sleeve, a handle fixed to said outer sleeve and an inner shaft. The inner shaft has a distal end with a torque driving tip. The inner shaft is coupled to the handle and axially movable relative to the outer sleeve from a proximal disengaged position to a distal engaged position. The outer sleeve has a bone fastener retaining distal end configured to lock into an internal groove or undercut of a bone fastener screw head when the inner shaft is axially moved from the proximal disengaged position to the distal engaged position to lock the bone fastener to the driver and upon a return movement of the inner shaft to the proximal disengaged position to unlock and release the driver from the bone fastener screw head.

5 Claims, 24 Drawing Sheets

(56) References Cited

U.S. PATENT DOCUMENTS

| | | | |
|---|---|---|---|
| 6,415,693 B1* | 7/2002 | Simon | A61B 17/8891 81/453 |
| 7,226,453 B2 | 6/2007 | Chao et al. | |
| 7,406,899 B1 | 8/2008 | Walker | |
| 7,452,361 B2 | 11/2008 | Kreidler | |
| 7,572,264 B2 | 8/2009 | Null et al. | |
| 8,343,165 B2* | 1/2013 | Berrevoets | A61B 17/8875 606/86 A |
| 8,394,108 B2 | 3/2013 | Mclean et al. | |
| 8,460,307 B2* | 6/2013 | Saidha | A61B 17/888 606/104 |
| 8,726,769 B1 | 5/2014 | Jacker | |
| 8,808,307 B2* | 8/2014 | Robinson | A61B 17/7032 606/104 |
| 8,869,659 B2* | 10/2014 | Chang | B25B 23/0021 81/177.85 |
| 8,951,264 B2 | 2/2015 | Saidha et al. | |
| 9,554,834 B2 | 1/2017 | Saidha et al. | |
| 9,924,980 B2 | 3/2018 | Saidha et al. | |
| 11,618,135 B2* | 4/2023 | Sharifi-Mehr | A61B 17/8886 81/32 |
| 2007/0005077 A1* | 1/2007 | Null | A61B 17/8883 606/104 |
| 2007/0270880 A1* | 11/2007 | Lindemann | A61B 17/8891 606/104 |
| 2008/0045970 A1* | 2/2008 | Saidha | A61B 17/7035 81/436 |
| 2008/0190252 A1* | 8/2008 | Parrott | A61B 17/8888 81/451 |
| 2008/0269768 A1* | 10/2008 | Schwager | B25B 23/108 81/436 |
| 2009/0326545 A1* | 12/2009 | Schaffhausen | A61B 17/8891 81/436 |
| 2010/0024608 A1* | 2/2010 | Chen | B25B 23/0057 81/177.85 |
| 2012/0215232 A1* | 8/2012 | Olsen | A61B 17/8888 606/139 |
| 2012/0247284 A1* | 10/2012 | Murray | A61B 17/8888 81/436 |
| 2012/0253355 A1* | 10/2012 | Murray | B25B 15/005 606/104 |
| 2012/0326399 A1* | 12/2012 | Lin | B25B 23/12 279/75 |
| 2013/0004916 A1* | 1/2013 | Bellanca | A61C 8/0057 433/173 |
| 2013/0068072 A1* | 3/2013 | Li | B25G 1/005 81/177.1 |
| 2013/0150864 A1* | 6/2013 | Marik | A61B 17/8888 606/104 |
| 2015/0202751 A1* | 7/2015 | Chen | B25B 23/0035 279/9.1 |
| 2016/0082577 A1* | 3/2016 | Sanders | B25B 15/008 81/452 |
| 2016/0327077 A1* | 11/2016 | Huang | B25B 23/0057 |
| 2017/0042600 A1* | 2/2017 | Ross | A61B 17/8888 |
| 2017/0303981 A1* | 10/2017 | Myers | A61B 17/8888 |
| 2018/0235684 A1* | 8/2018 | Hawkes | B25B 23/108 |
| 2019/0029737 A1* | 1/2019 | Wall | A61B 17/86 |
| 2020/0188004 A1* | 6/2020 | Flores | A61B 17/8886 |
| 2021/0045791 A1* | 2/2021 | Perrow | B25B 15/02 |

* cited by examiner

BONE FASTENER AND DRIVER WITH RETAINING FEATURES

FIELD OF THE INVENTION

The present invention relates to a bone fastener and driver with fastener retaining features to facilitate installation.

BACKGROUND OF THE INVENTION

Bone fasteners or screws have a threaded shank and a screw head with a torqueing aperture to connect a screw driver with a male driving feature to turn the screw into bone. In some cases, the shank has thread cutting flutes to create a threaded attachment into the bone, these screws are often referred to as self-tapping. Other times, the bone has been pre-drilled prior to inserting the fastener. Regardless of form or type used, it is important the bone fastener stay firmly and securely affixed to the driver while being inserted into the bone. If the fastener separates and is dislodged from the driver, the surgeon must recover the fastener lying loose and often hidden from view by the tissue of the patient. Accordingly, great care is taken to avoid this problem.

Ideally, the bone fastener has an enlarged head extending at a proximal end of the threaded shank. The bone fastener head can be polyaxially configured with a hemispherical lower portion. This allows the fastener to be driven through a bone plate or other device being implanted on an angle. At the very proximal end of the bone fastener is a torqueing aperture which can be a star, square or hexagonal female opening configured to receive a male tip of a driver. While designed for a close-fitting arrangement, the driver and complimentary fastener are easily separated. This leads to the problem of separation during installation.

The present invention provides drivers and bone fasteners that have a secure locking attachment that eliminates this issue while providing a simple and quick release after implanted as described hereinafter.

SUMMARY OF THE INVENTION

A bone fastener driver assembly with a bone fastener retention feature has an outer sleeve, a handle fixed to said outer sleeve and an inner shaft. The inner shaft has a distal end with a torque driving tip. The inner shaft is coupled to the handle and axially movable relative to the outer sleeve from a proximal disengaged position to a distal engaged position. The outer sleeve has a bone fastener retaining distal end configured to lock into an internal groove or undercut of a bone fastener screw head when the inner shaft is axially moved from the proximal disengaged position to the distal engaged position to lock the bone fastener to the driver and upon a return movement of the inner shaft to the proximal disengaged position to unlock and release the driver from the bone fastener screw head.

The handle has one or more ball detents configured to engage a pair of positioning grooves, a proximal groove on the inner shaft positioned to fix axially the proximal disengaged position and a distal groove spaced distally relative to the proximal groove positioned to fix axially the distal engaged position. The inner shaft when in the distal engaged position is configured to engage a torqueing aperture inside the bone fastener screw head as the outer shaft is locked into the internal groove or undercut of the bone fastener screw head and when the inner shaft is in the proximal disengaged position the outer shaft is unlocked from the internal groove and the driver can be disengaged from the bone fastener screw head. The bone fastener driver assembly further has one or more bone fasteners. Each bone fastener has the bone fastener screw head with an internal groove or undercut.

In one embodiment, the bone fastener driver assembly one or more bone fasteners each have a proximal end with a plurality of flexible fingers above the internal groove or undercut configured to flex outwardly to attach onto an internal ring on the outer sleeve to attach the driver to the bone fastener screw head.

In another embodiment, the bone fastener driver assembly outer sleeve has a plurality of flexible fingers at the distal end of the outer sleeve and each of the one or more bone fasteners has the bone fastener screw head with an internal groove or undercut to receive the outer sleeve. Each flexible finger has a projecting end configured to clip into the internal groove or undercut of the bone fastener screw head as the flexible fingers flex inwardly toward the inner shaft to engage the bone fastener screw head and spring lock as the projecting ends enter the internal groove or undercut locking the bone fastener screw head to the driver when the inner shaft is positioned in the distal engaged position.

In another embodiment, the bone fastener driver assembly outer sleeve has a distal external groove configured to hold a split ring; and a split ring held in the distal external groove and protruding radially outwardly. The split ring is compressible and configured to compress on entry into the bone fastener screw head and upon aligning with the internal groove or undercut springs outwardly to attach the outer sleeve to the bone fastener and lock thereto when the inner shaft is moved to the distal engaged position. The bone fastener driver outer shaft when the inner shaft is moved to the proximal disengaged position, the split ring compresses as it flexes and is released from the bone fastener screw head.

BRIEF DESCRIPTION OF THE DRAWINGS

The invention will be described by way of example and with reference to the accompanying drawings in which.

DETAILED DESCRIPTION OF THE INVENTION

With reference to FIGS. 1-33, bone fasteners and driver assemblies of the present invention are illustrated. All of the various embodiments shown use a bone fastener retaining feature that secures the head of the bone fastener to the driver in a secure locked engaged configuration and also provides an easy to use unlocking feature to release the driver from the bone fastener. As illustrated, each embodiment allows a surgeon to fasten an implant such as a lumbar plate with bone fasteners without the risk of the fastener dislodging or coming off the driver during implantation. Equally importantly, once the fastener is threaded securely to the bone, the driver can be unlocked from the bone fastener easily without risking loosening the fastener from the bone.

Figure 1:
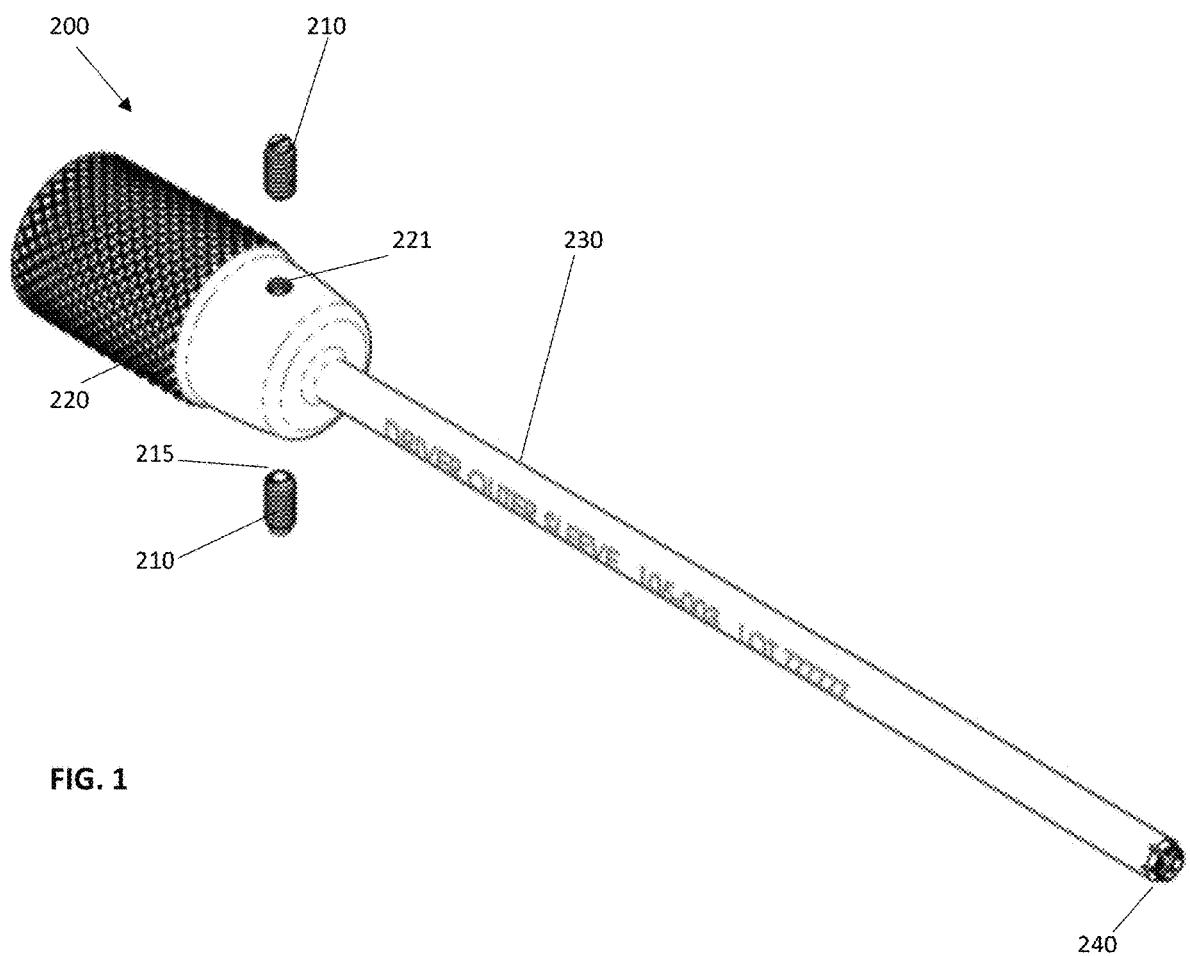
FIG. 1 is a perspective view of the driver outer sleeve of the present invention.

With reference to FIGS. 1-12, the bone fastener driver assembly 200 of the present invention is illustrated. With reference to FIG. 1, the outer sleeve 230 of the driver assembly 200 is illustrated. The outer sleeve 230 is integrally attached to a handle 220 at a proximal end and has a bone fastener screw head retention feature 240 at the distal end. The handle 220 as illustrated has knurled outer surfaces to facilitate rotating the handle when gripped by the surgeon.

Figure 2:
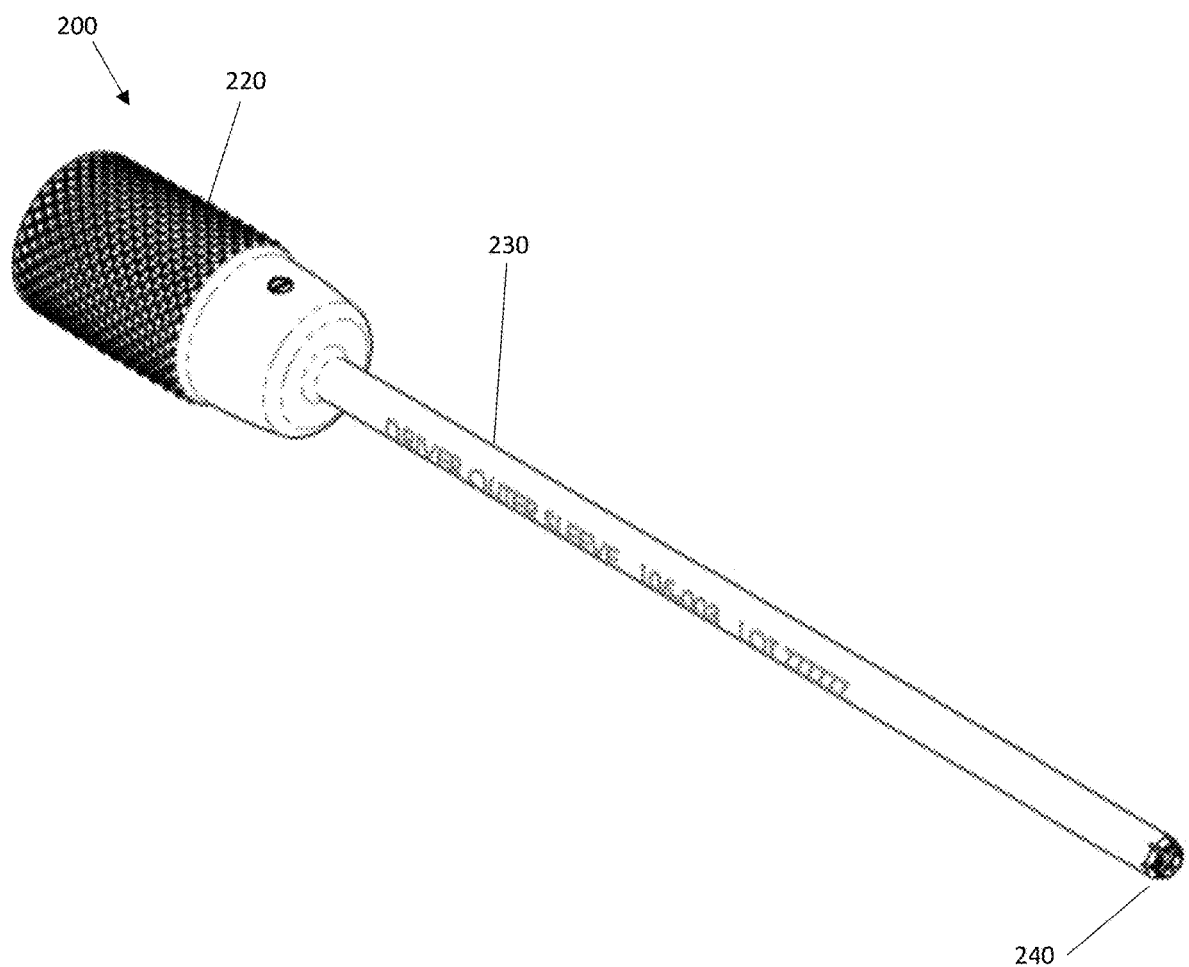
FIG. 2 is a perspective view of the driver outer sleeve assembled with the shaft holding ball detent fasteners installed in the handle.

As shown in the exploded view, threaded detent pins 210 are illustrated above and below the handle for entry into openings 221 in the handle 220. These detent pins 210 have a spring loaded detent ball 215 and when threaded into the openings 221 will be used for securing another feature that is inserted through the hollow outer sleeve 230 of the driver assembly 200. FIG. 2 shows the detent pins 210 installed into the handle 220 of the driver assembly 200.

Figure 3:
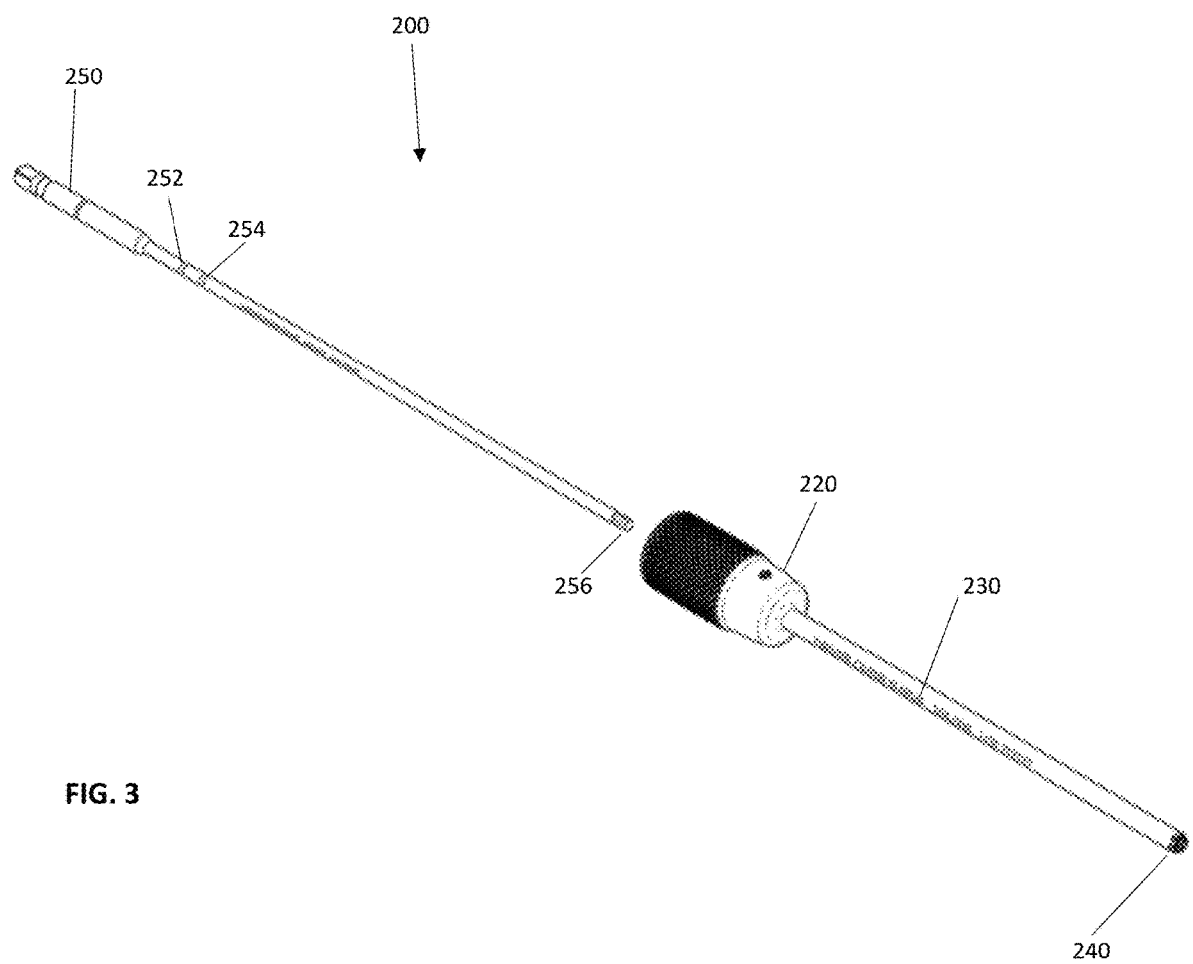
FIG. 3 shows the driver assembly with one inner shaft and outer sleeve in an exploded view.
Figure 4:
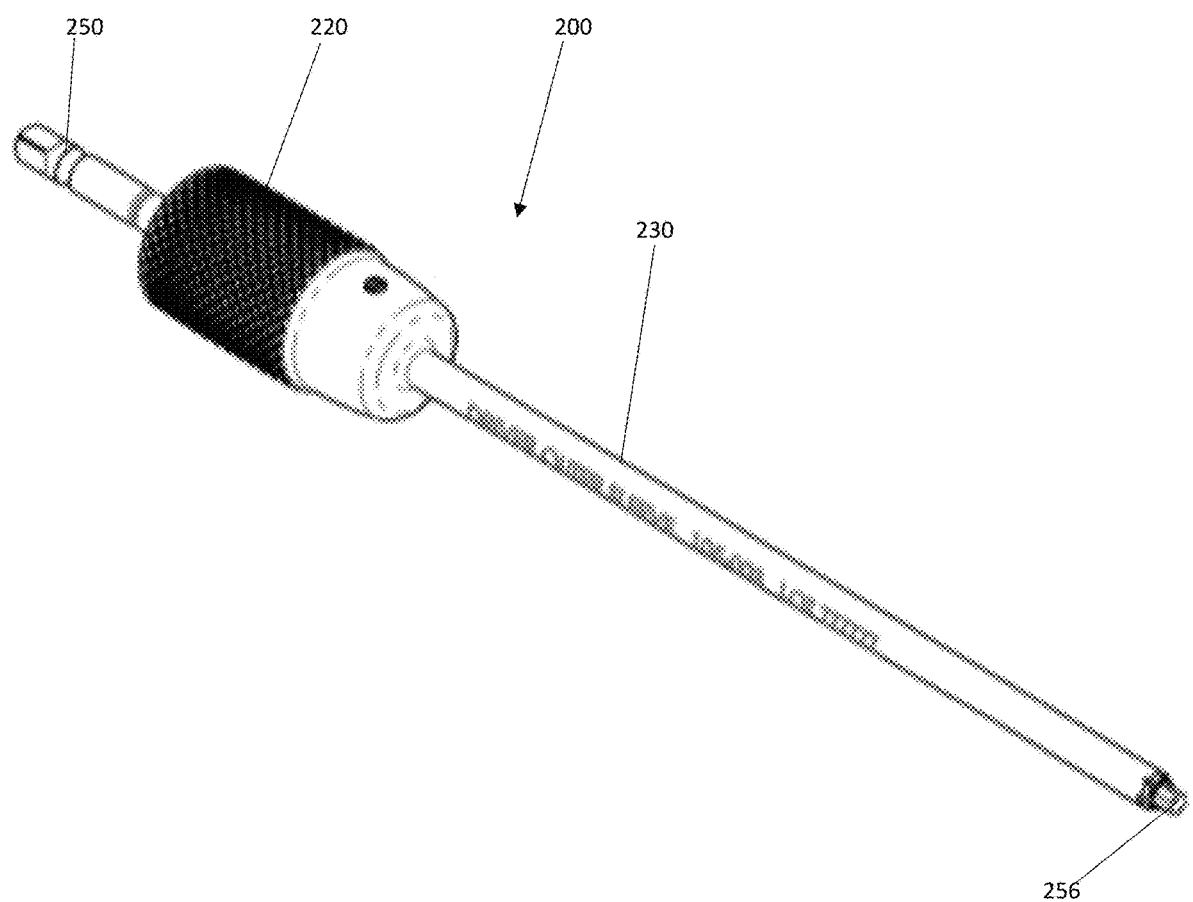
FIG. 4 shows the driver assembly with the inner shaft and outer sleeve in a forward engaged position.

With reference to FIG. 3, an inner shaft 250 is shown. The inner shaft 250 has a distal end with a torque engaging tip 256 configured to fit into a complimentary aperture of a bone fastener screw head and is a torqueing feature that allows the inner shaft 250 to rotate the bone fastener screw upon implantation. As shown, the elongated inner shaft 250 has a pair of grooves, one distal groove 254 and one proximal groove 252 that are spaced apart axially by a fixed distance on the inner shaft 250. This inner shaft 250 fits through the handle 220 and into the outer sleeve 230, as shown in FIG. 4.

Figure 5A:
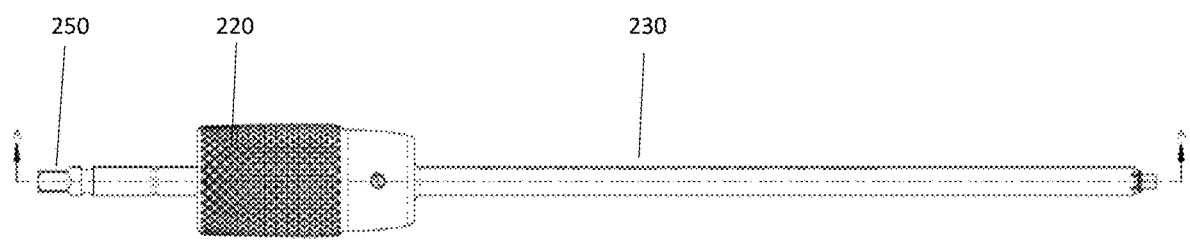
FIG. 5A is a plan view of the driver assembly inner shaft and outer sleeve with the driver in the forward engaged position.
Figure 5B:
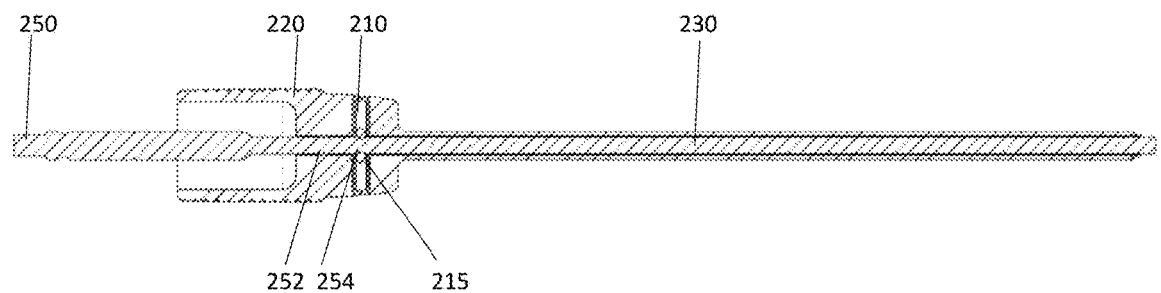
FIG. 5B is a cross sectional view taken along line A-A of FIG. 5A.
Figure 6:
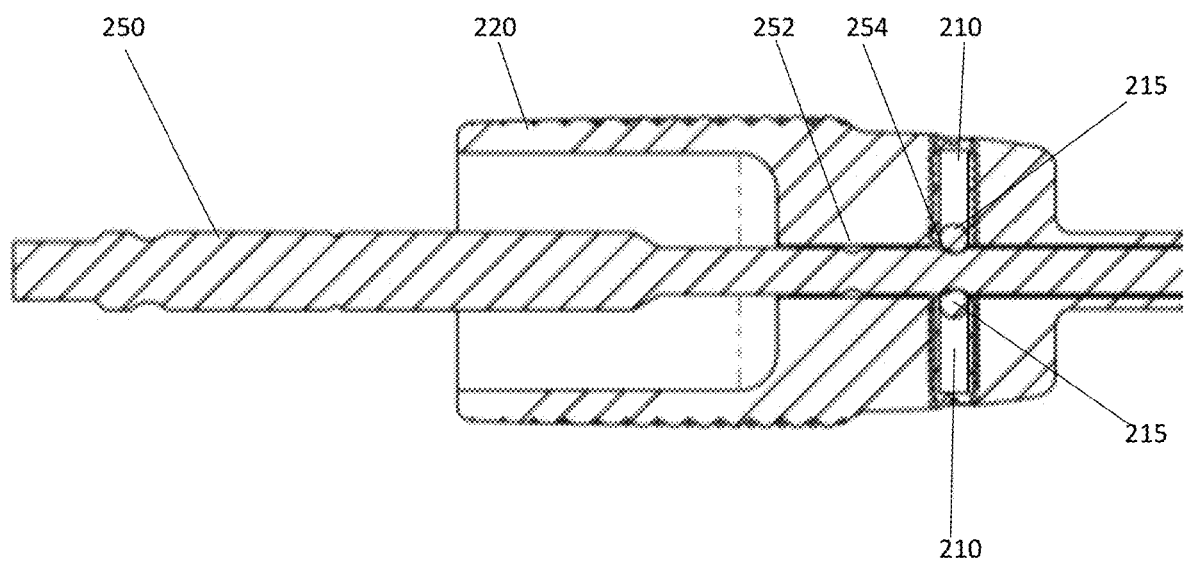
FIG. 6 is an enlarged cross sectional view of the forward engaged position with the ball detents holding the inner shaft.

As further shown in FIGS. 5A and 5B, the inner shaft 250 when positioned inside the handle 220, as best shown in the cross-sectional view of FIG. 5B, the detent pins 210 with detent balls 215 are shown engaged into the distal groove 254. This distal positioning of the inner shaft 250 as shown fixes the tip 256 of the inner shaft 250 relative to the outer sleeve 230 distal end. FIG. 6 is an enlarged view showing the detent ball 215 into the groove 254 as previously discussed. When the detent balls 215 are in the distal groove 254, the tip end 256 is shown moved closer to the outer sleeve 230 distal end 240 such that there is little space between the end of the outer sleeve 230 and the tip 256, as illustrated. This is considered the distal engaged position.

Figure 7:
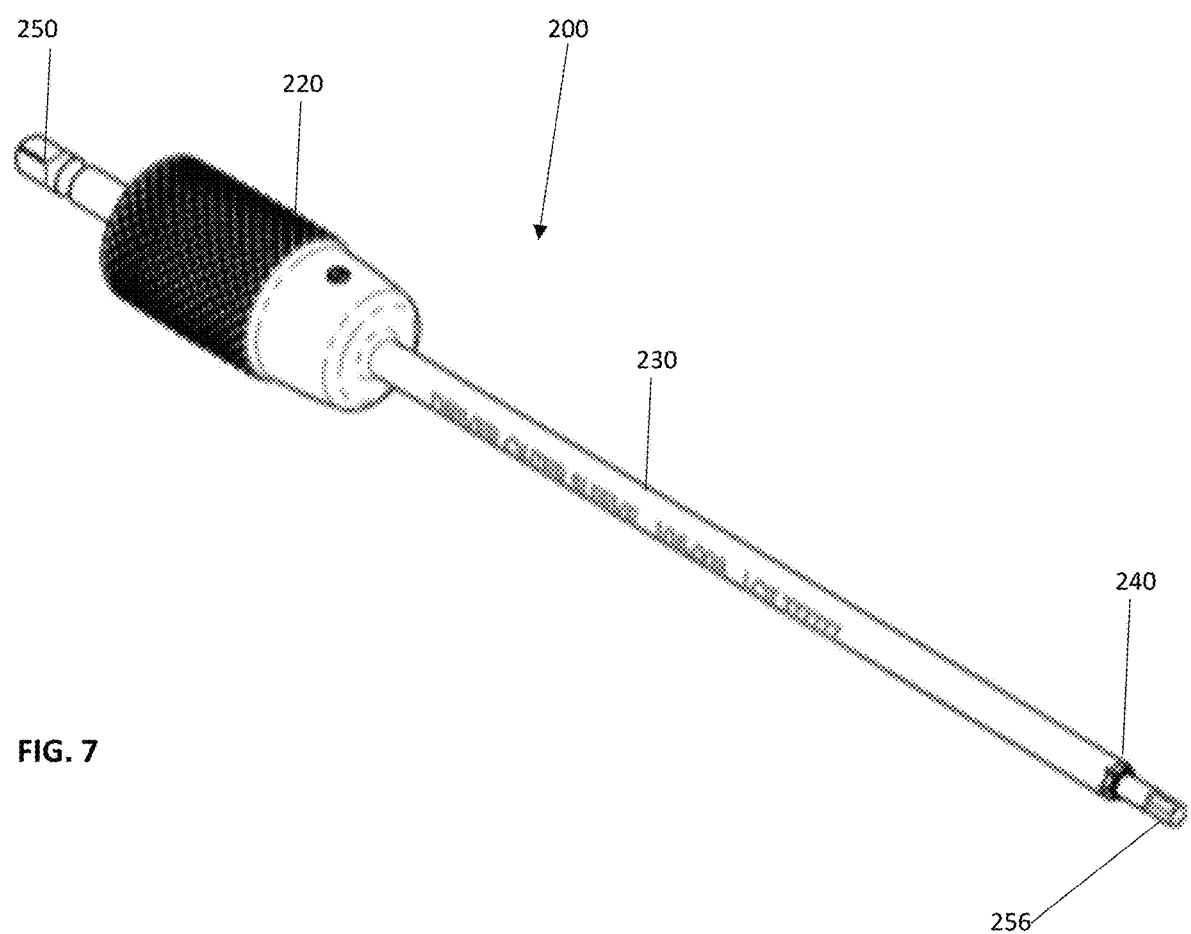
FIG. 7 is a perspective view of the driver assembly with inner shaft and outer sleeve shown in a rearward disengaged position.
Figure 8A:
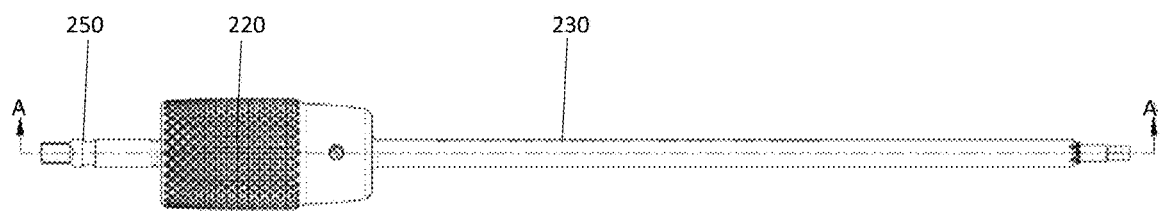
FIG. 8A shows the driver assembly with inner shaft and outer sleeve in a top or plan view with the driver in the rearward disengaged position.
Figure 8B:
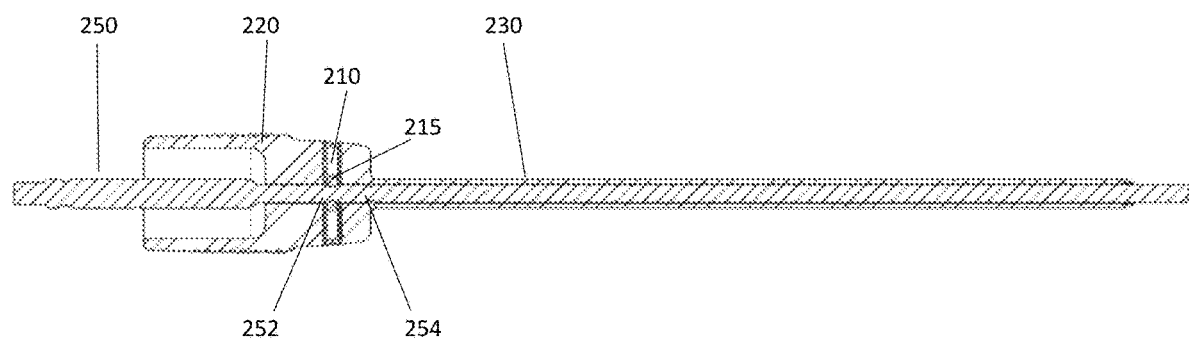
FIG. 8B is a cross sectional view taken along line A-A of FIG. 8A.
Figure 9:
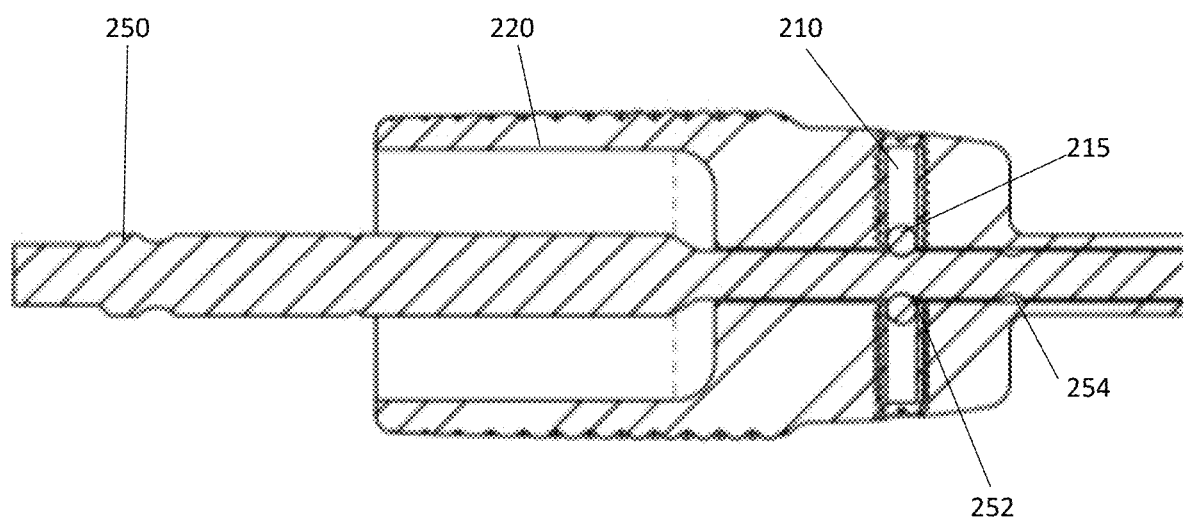
FIG. 9 is an enlarged view of the rearward disengaged position with ball detents.
Figure 10A:
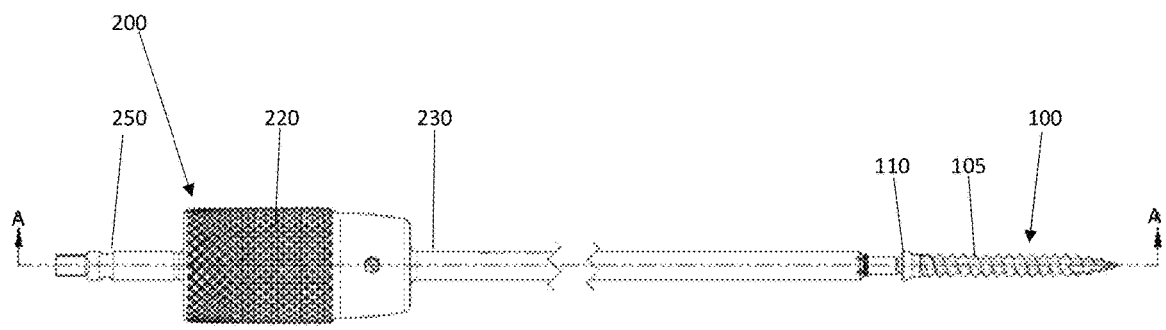
FIG. 10A is a plan view of the driver assembly with bone fastener attached with the driver in rearward disengaged position.
Figure 10B:
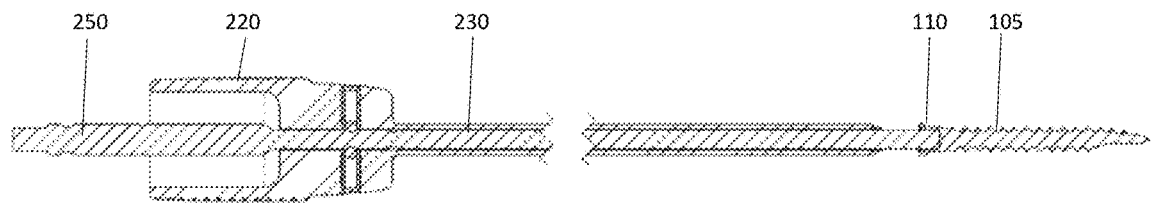
FIG. 10B is a cross sectional view taken along line A-A of FIG. 10A.

With reference to FIG. 7, the driver assembly is shown in the proximal disengaged position. When the detent balls 215 are in the proximal groove 252, the tip end 256 is shown moved distally away from the outer sleeve 230 distal end 240 such that there is space between the end of the outer sleeve 230 and the tip 256, as illustrated. This is considered the proximal disengaged position. As can be seen, the inner shaft 250 is forwardly positioned relative to the outer sleeve 230. In this configuration, as shown in FIGS. 8A and 8B, the tip 256 of the inner shaft 250 for providing torque is fully exposed. With reference to FIG. 9, the inner shaft 250 can be pulled proximally such that the detent balls 215 engage the proximal groove 252 of the inner shaft 250. When this occurs, the tip 256 will be in a position as shown in FIGS. 10A and 10B showing the bone fastener 100 detached from the outer sleeve 230 in the proximal disengaged position.

Figure 11A:
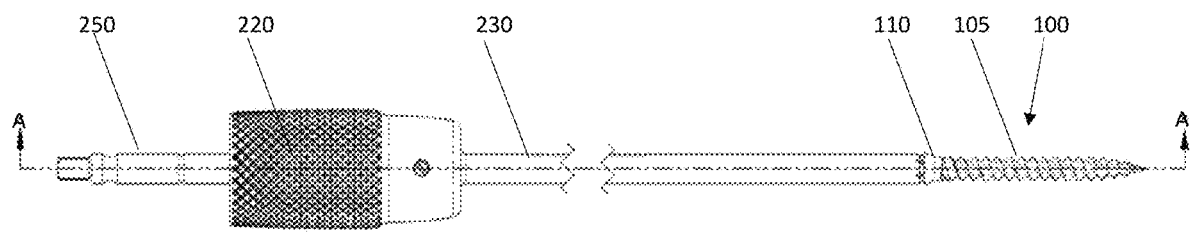
FIG. 11A is a plan view of the driver assembly with bone fastener attached and the driver in forward engaged position.
Figure 11B:
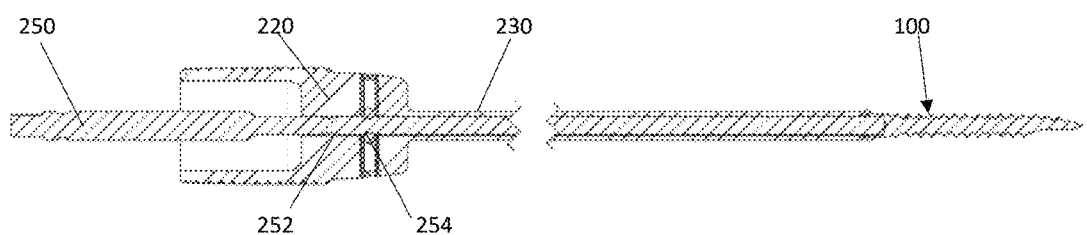
FIG. 11B is a cross sectional view of FIG. 11A taken along line A-A.
Figure 12:
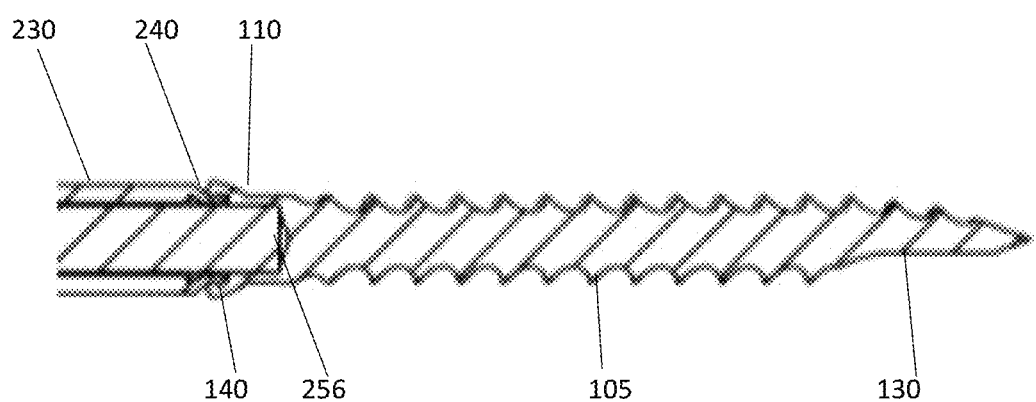
FIG. 12 is an enlarged plan view showing the locking fingers engaged in the bone fastener undercut groove.
Figure 13:
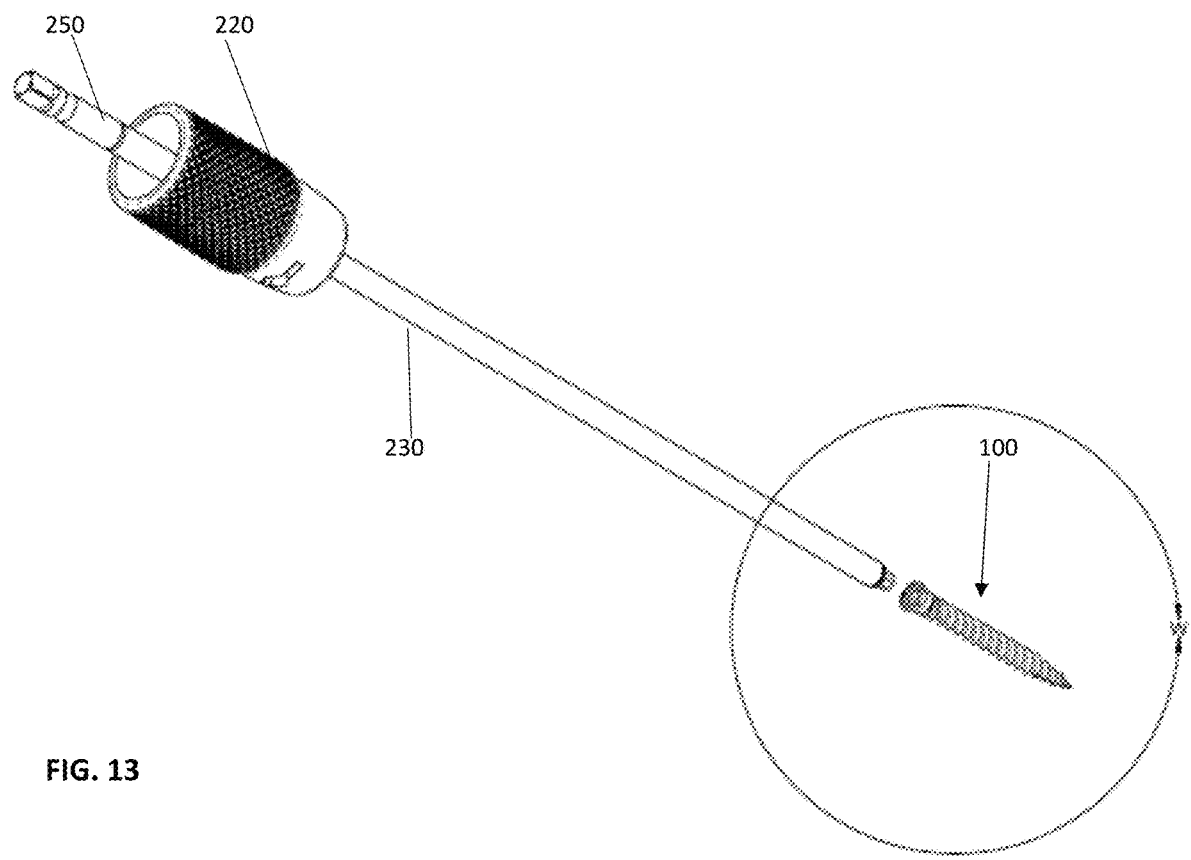
FIG. 13 is a perspective view of the driver and a bone fastener separated, the bone fastener is of a first embodiment.
Figure 14:
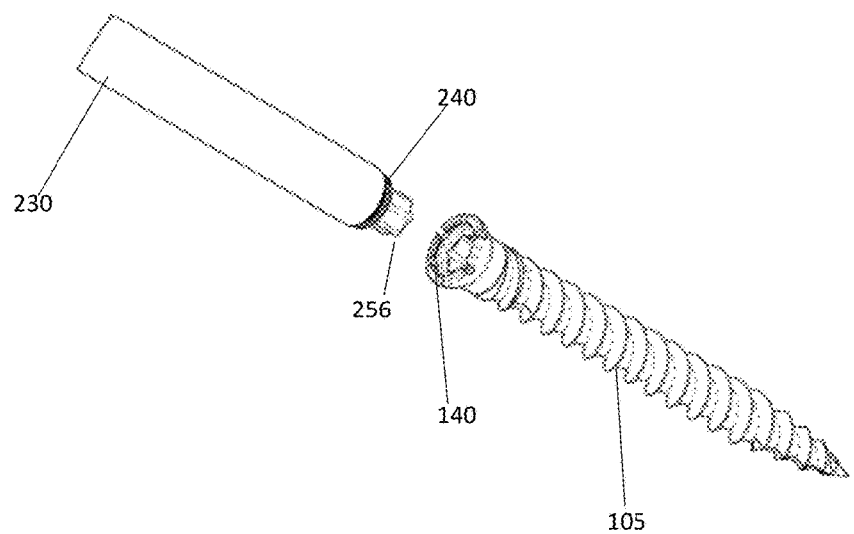
FIG. 14 is an enlarged view taken from FIG. 13.

Initially the bone fastener screw head 110 is positioned with the driver aperture 120 of the bone fastener 100 placed over the male tip 256 of the inner shaft 250, the inner shaft 250 has been pulled proximally back to the distal engaged position and the locking feature 140 is attached to the outer sleeve 230 bone fastener retaining distal end 240 as shown in FIGS. 11A and 11B and as best illustrated in FIG. 12. When this occurs, the locking or retaining features of the fastener and the driver are fully engaged and the bone fastener 100 can not be dislodged easily from the assembly 200 until the driver outer sleeve 230 and inner shaft 250 are moved into the proximal disengaged position.

With reference to FIGS. 13-19, a first embodiment of the invention is shown. In this embodiment, the outer sleeve 230 bone fastener retaining distal end 240 has a locking groove 241 such that the bone fastener 100 when fitted onto the tip 256 of the inner shaft 250 locks onto the bone fastener head 110 that has flexible fingers 140 with a plurality of slots longitudinally extending to provide flexing, these slots have a projection at the proximal end of the bone fastener screw head 110 formed by the groove or undercut 141 in such a way that the fingers 140 will flex outwardly when installed over the outer sleeve distal end 240 and into the groove 241 of the outer sleeve distal end 240. This is best illustrated in FIGS. 15A and 15B.

Figure 15A:
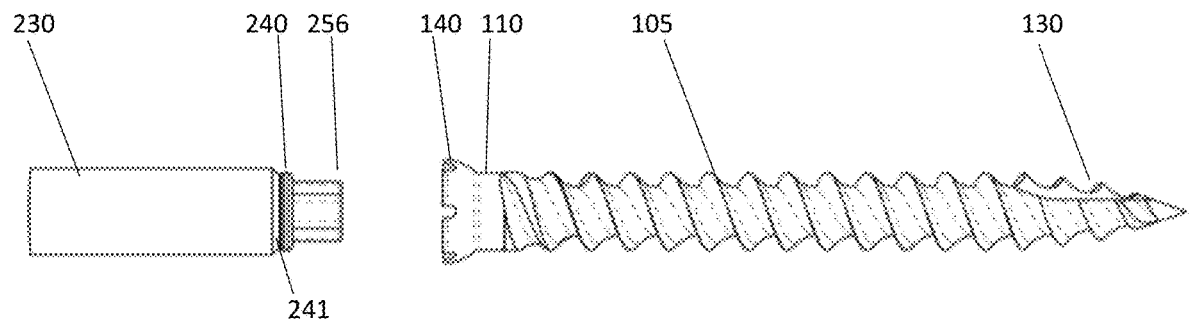
FIG. 15A is a side view showing the fingers on a first embodiment bone fastener head.
Figure 15B:
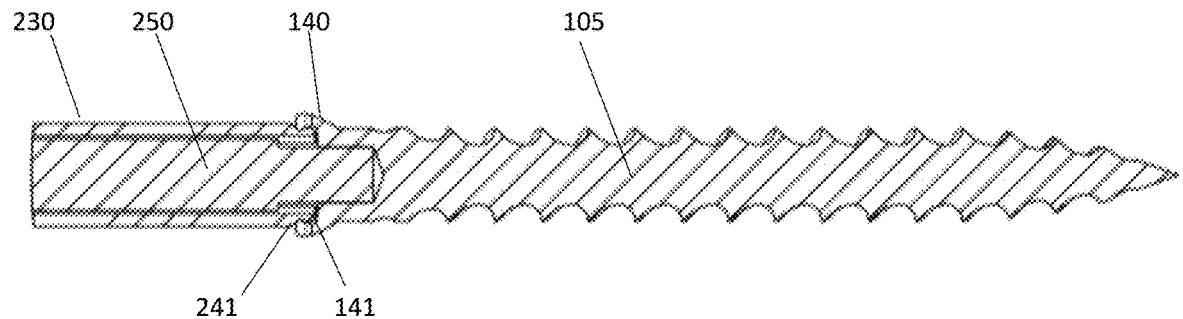
FIG. 15B is a cross sectional view showing the fingers clipped onto the outside of the driver sleeve.
Figure 16:
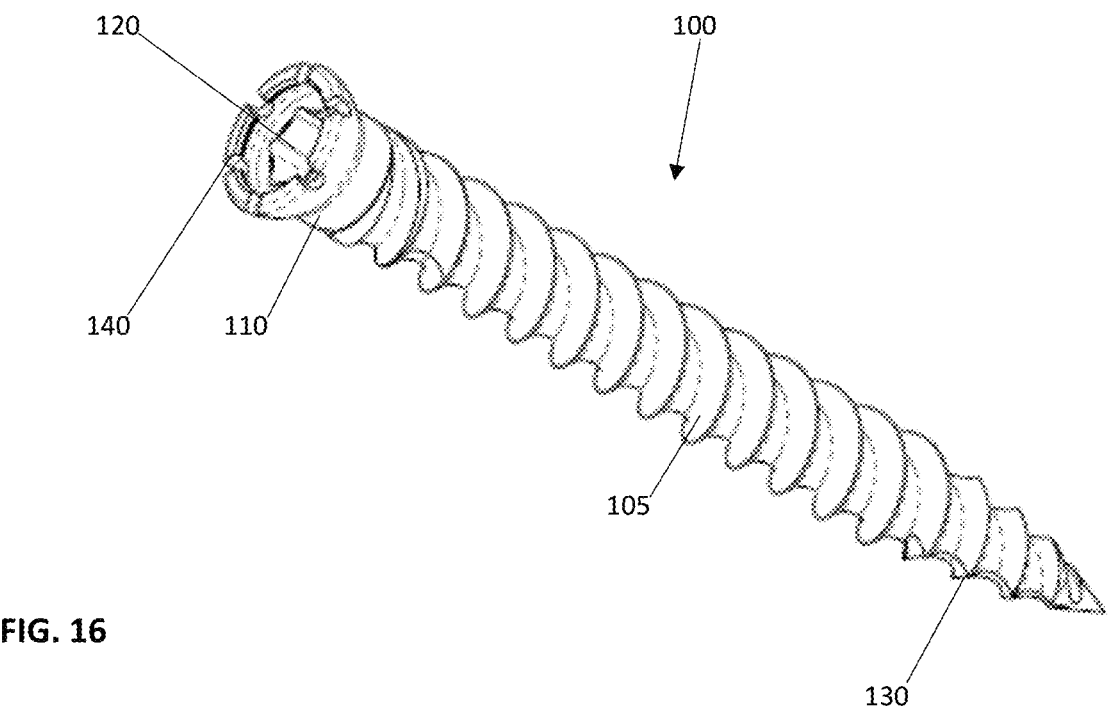
FIG. 16 is a perspective view of the first embodiment bone fastener of FIG. 14.
Figure 17:
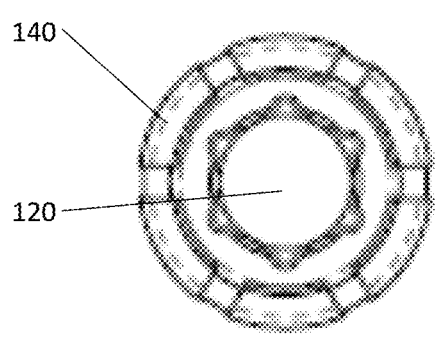
FIG. 17 is an end view of the first embodiment bone fastener.

When the bone fastener 100 is inserted onto the tip 256 a complimentary male tip is provided so the opening or aperture 120 of the screw head 110 can fit snugly onto the driver assembly 200. As the screw head 110 is moved onto the tip 256, the fingers 140 flex outwardly clip onto the outer sleeve 230 to lock onto the driver assembly 200. This is shown in FIG. 15B when the inner shaft is moved to the distal engaged position.

Figure 18:
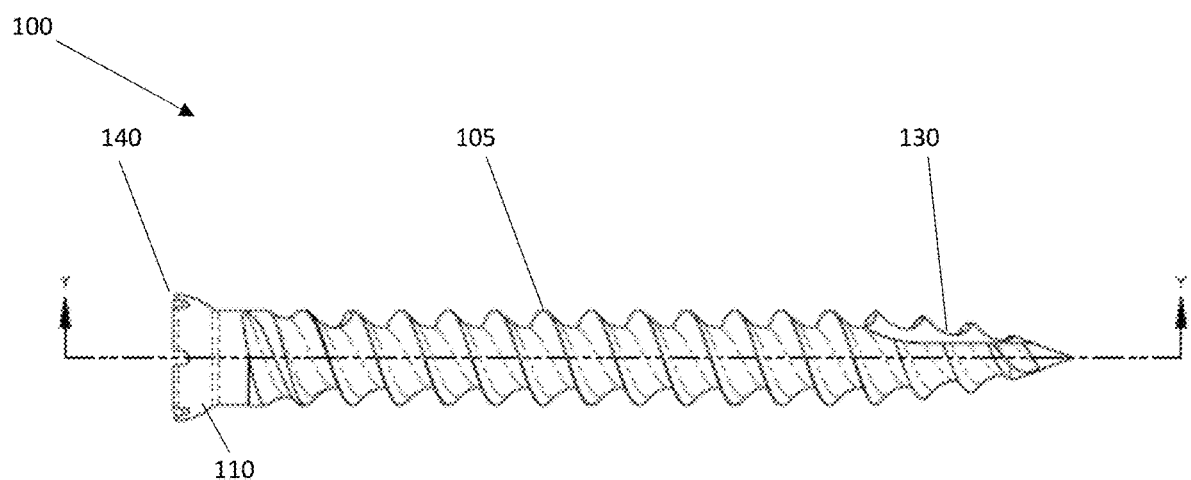
FIG. 18 is a plan view of the first embodiment bone fastener.
Figure 19:
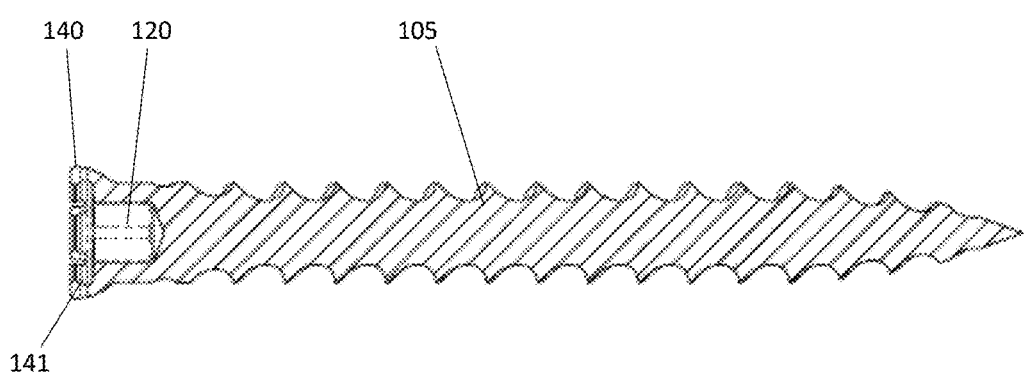
FIG. 19 is a cross-sectional view taken along line Y-Y of FIG. 18 of the first embodiment bone fastener.
Figure 20:
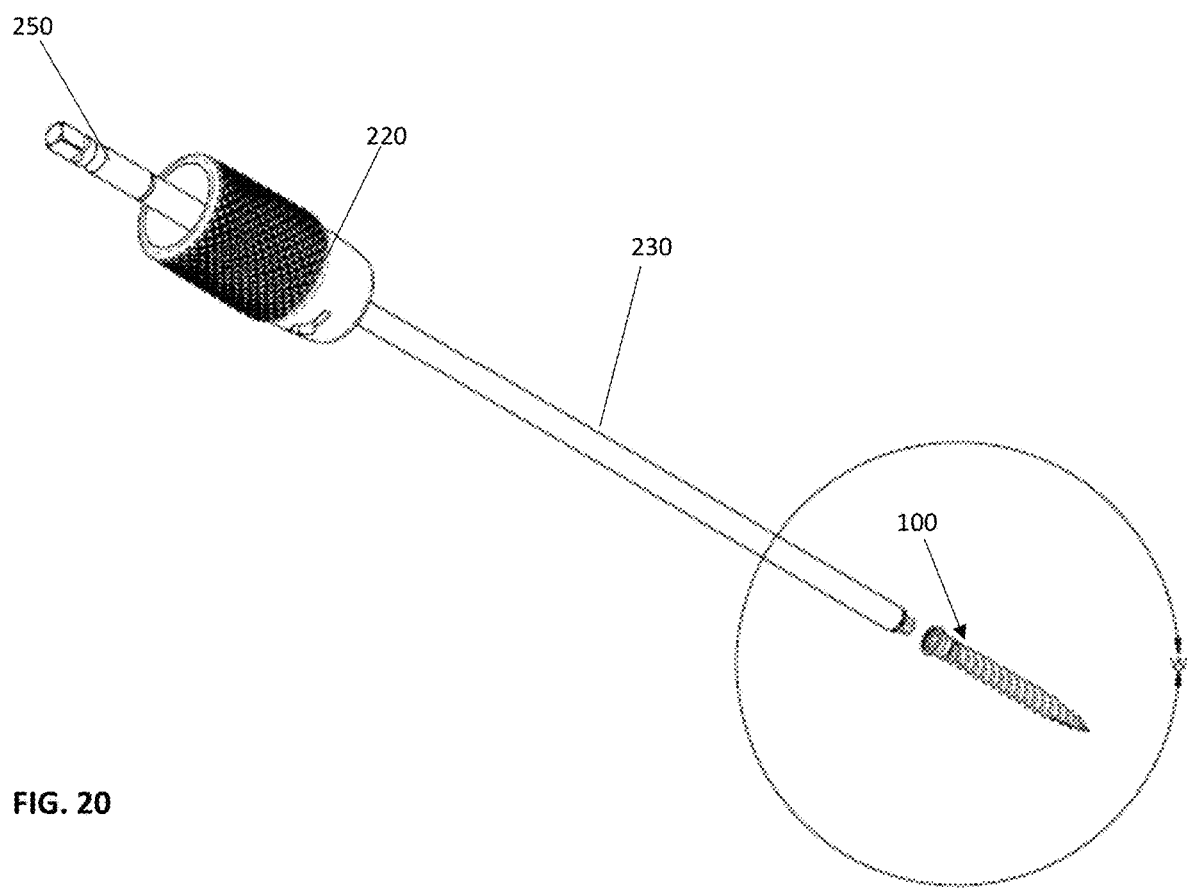
FIG. 20 is a drive assembly and a bone fastener of a second embodiment.
Figure 21:
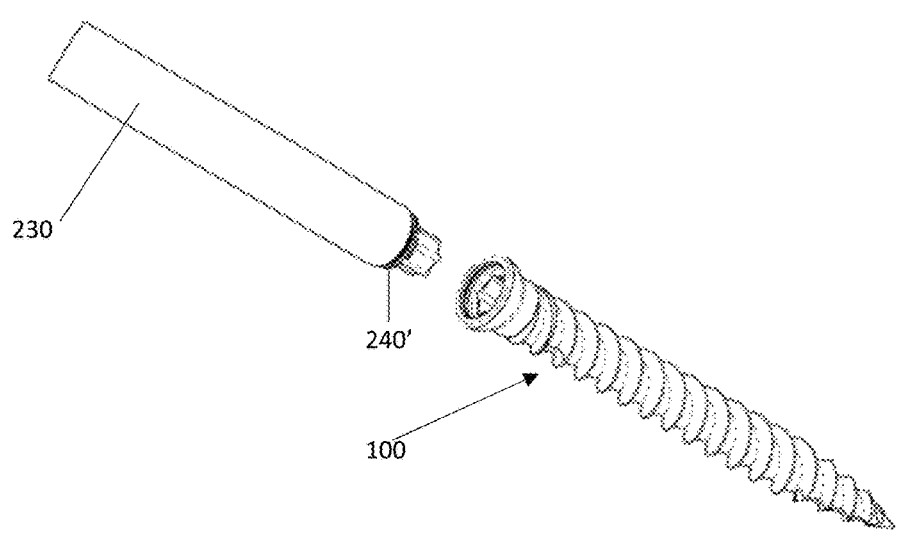
FIG. 21 is an enlarged view taken from FIG. 20.
Figure 22A:
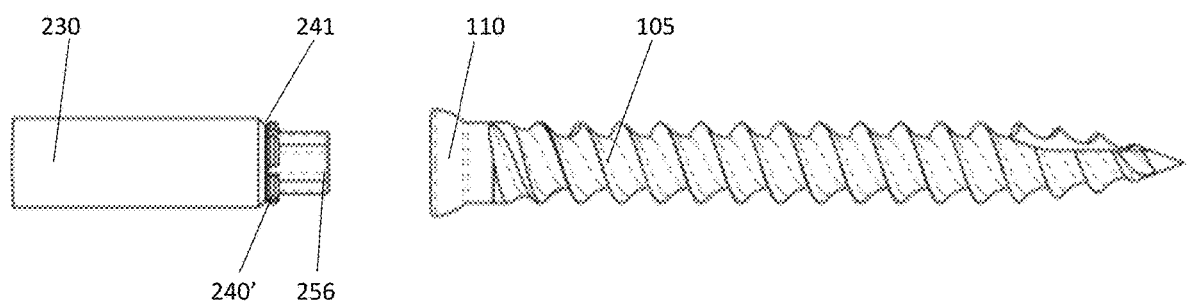
FIG. 22A is a side view showing fingers on the outer sleeve of the driver.
Figure 22B:
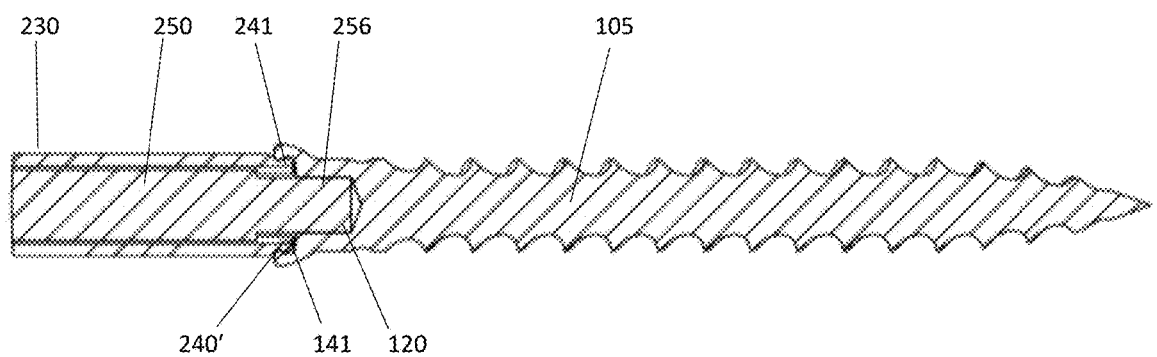
FIG. 22B is a cross sectional view showing the fingers clipped into the undercut groove on the bone fastener.
Figure 23:
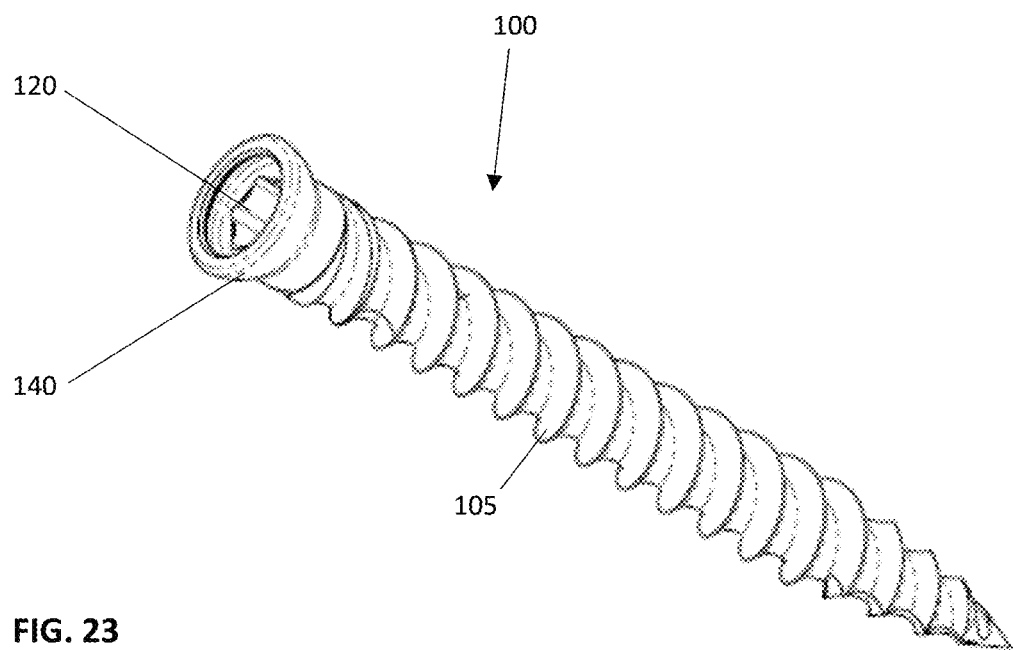
FIG. 23 is a perspective view of the second embodiment bone fastener of FIG. 20.
Figure 24:
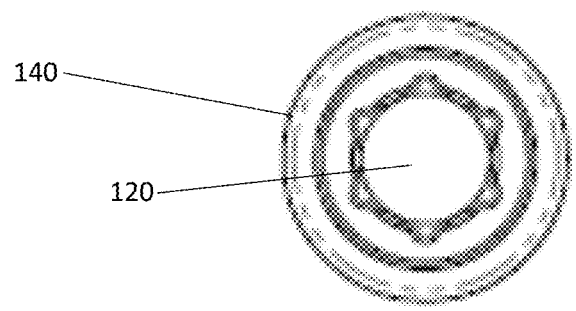
FIG. 24 is an end view of the second embodiment bone fastener.
Figure 25:
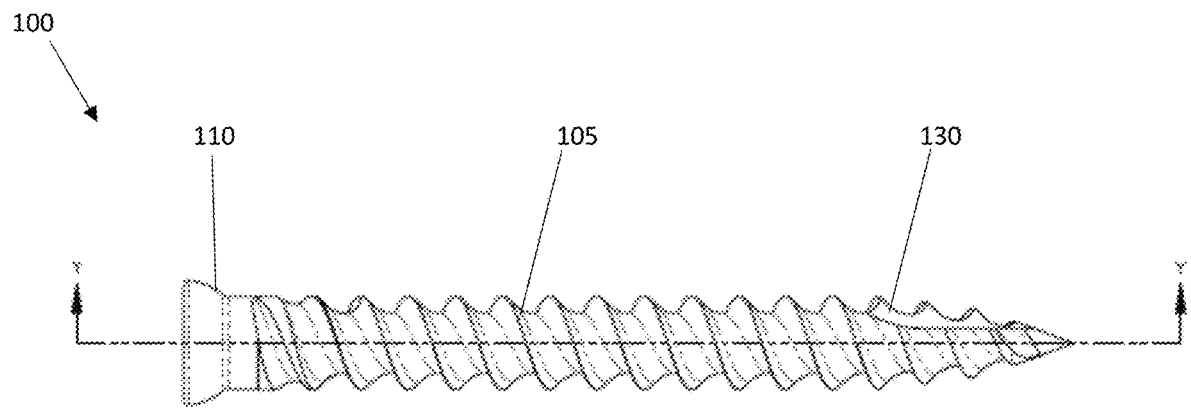
FIG. 25 is a plan view of the second embodiment bone fastener.
Figure 26:
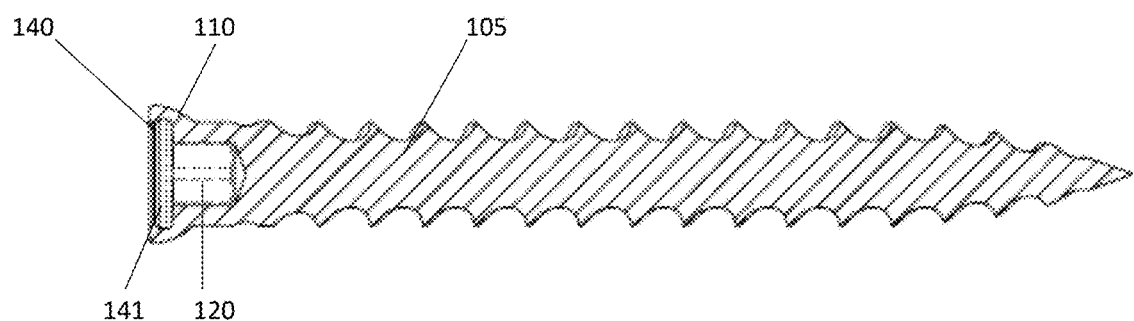
FIG. 26 is a cross-sectional view taken along line Y-Y of FIG. 25 of the second embodiment bone fastener.
Figure 27:
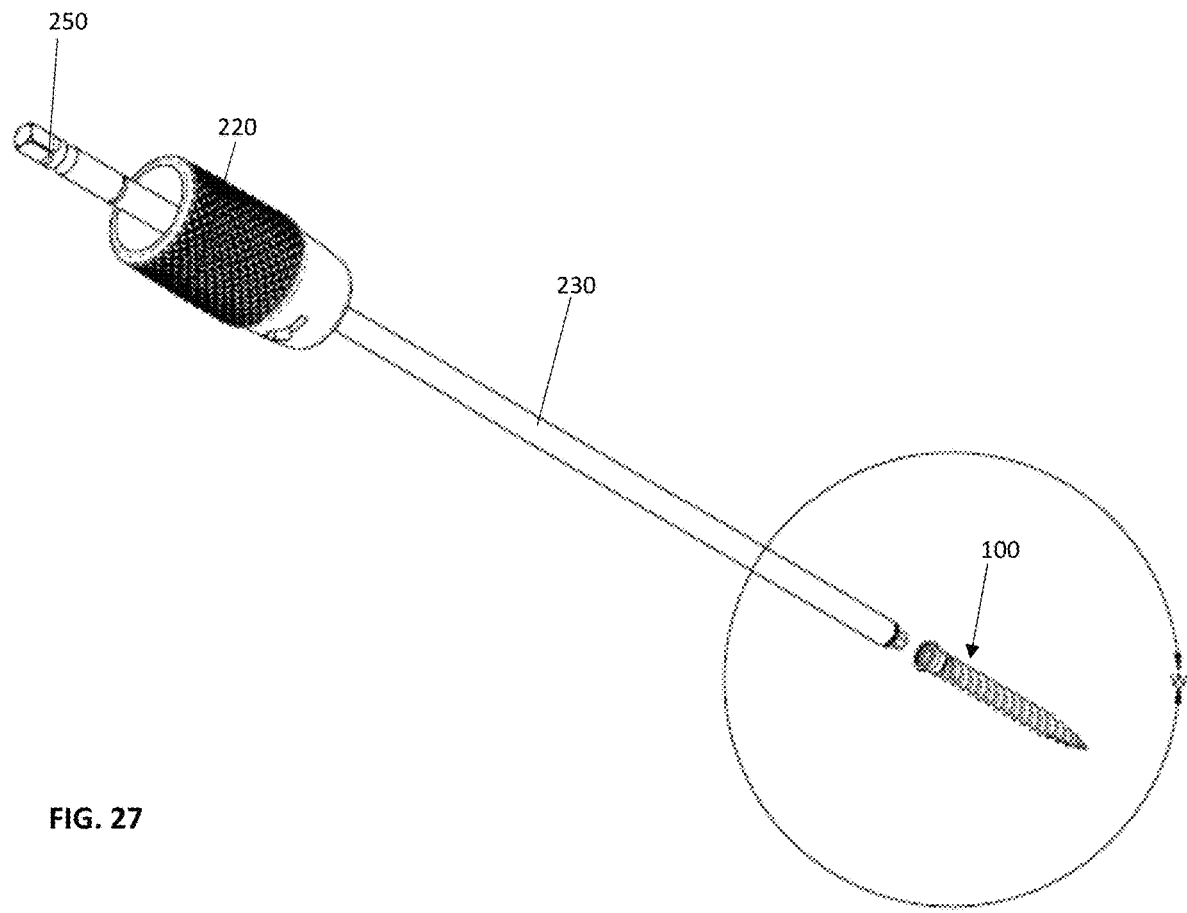
FIG. 27 is a drive assembly and a bone fastener of a third embodiment.
Figure 28:
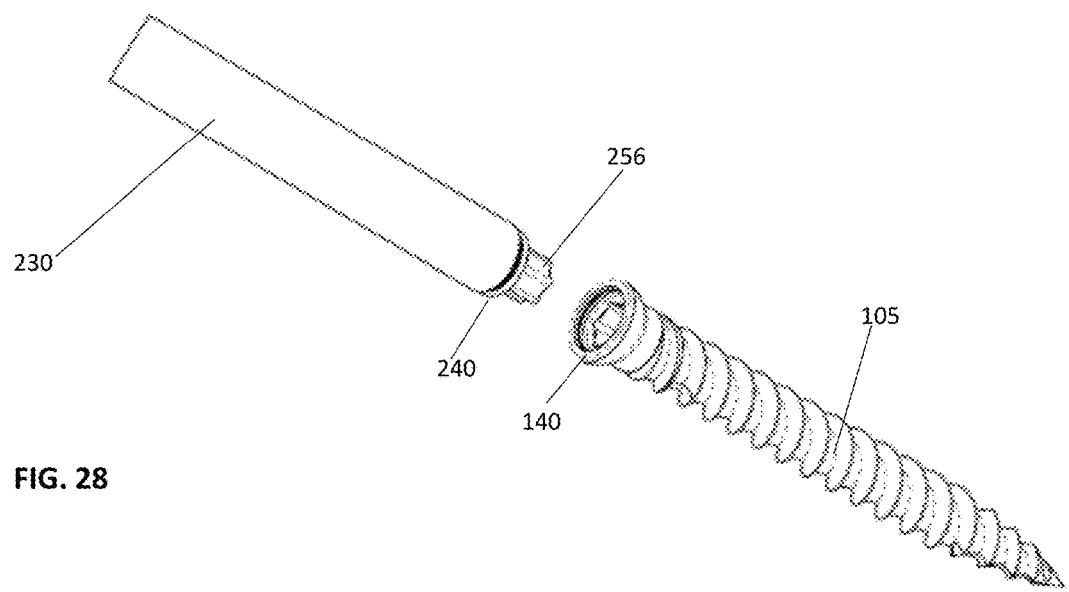
FIG. 28 is an enlarged view taken from FIG. 27.
Figure 29A:
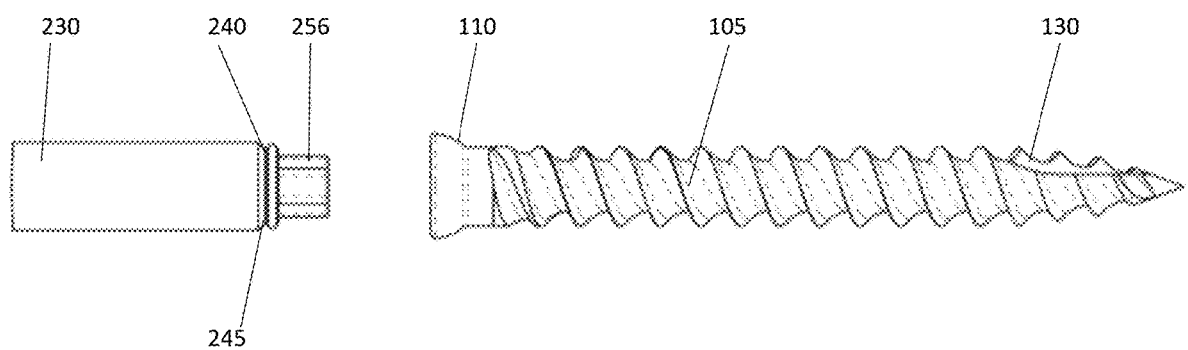
FIG. 29A is a side view showing the split ring on the outer sleeve of the driver.
Figure 29B:
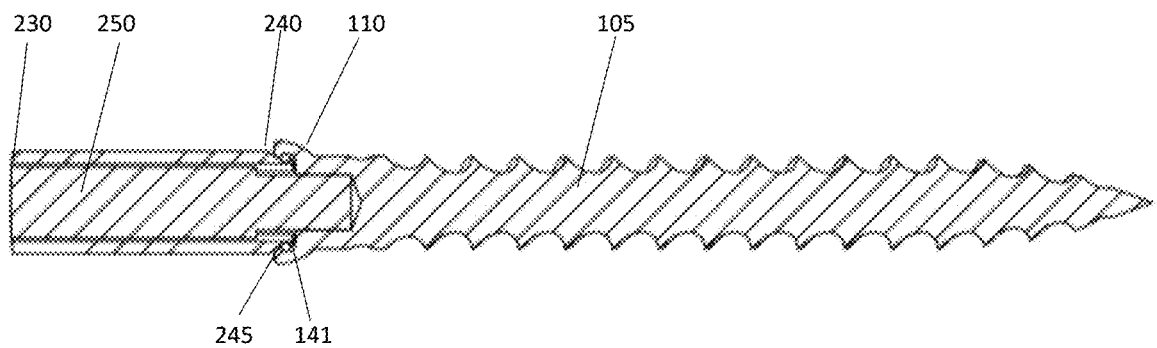
FIG. 29B is a cross sectional view showing the split ring clipped into the undercut groove on the bone fastener head.
Figure 30:
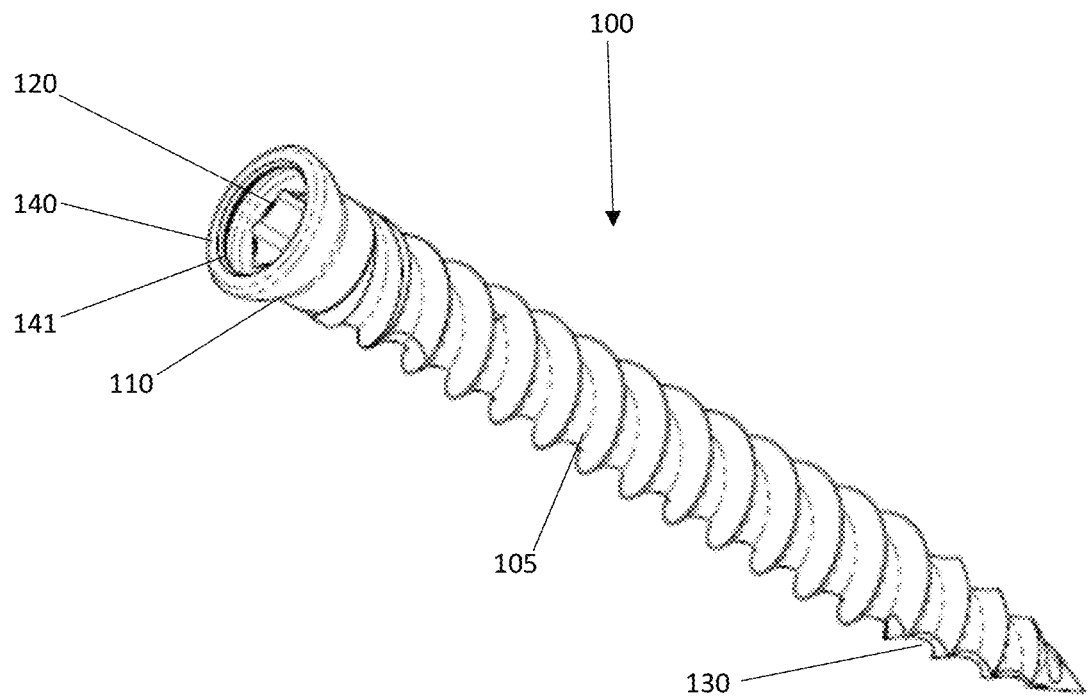
FIG. 30 is a perspective view of the third embodiment bone fastener of FIG. 27.
Figure 31:
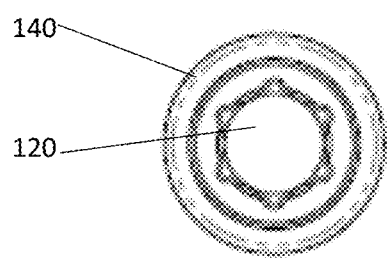
FIG. 31 is an end view of the third embodiment bone fastener.
Figure 32:
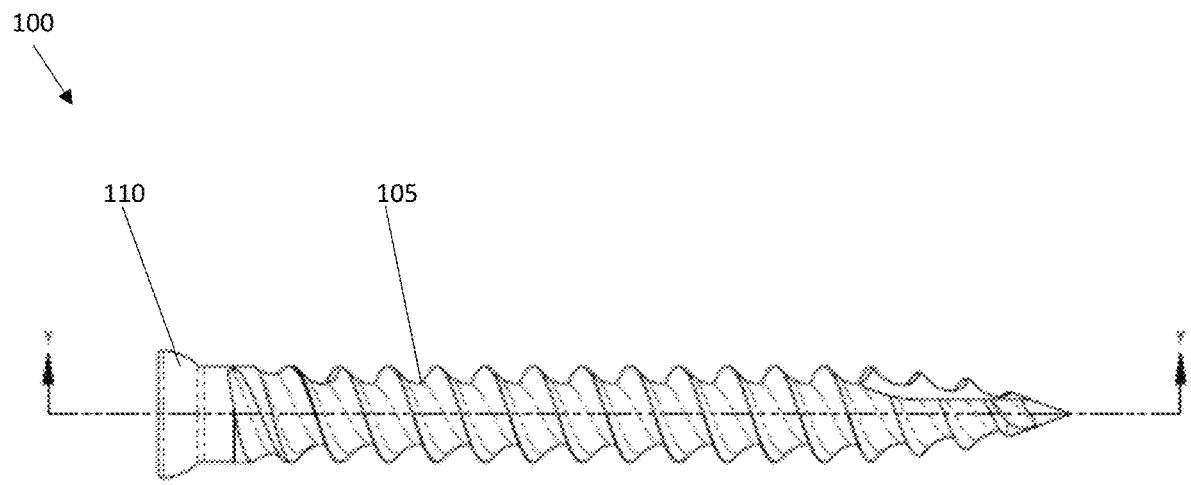
FIG. 32 is a plan view of the third embodiment bone fastener.
Figure 33:
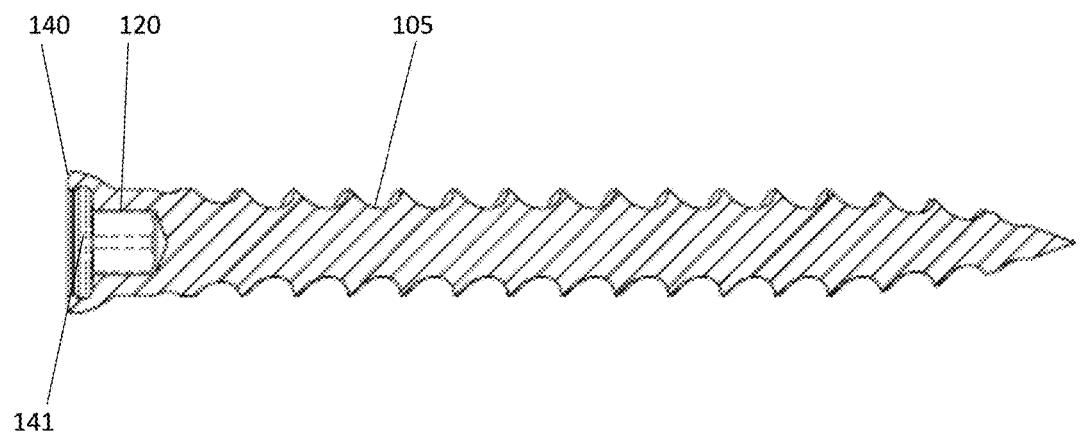
FIG. 33 is a cross-sectional view of the third embodiment bone fastener.

FIGS. 18 and 19 simply show a plan view and cross-sectional view of the bone fastener 100 with threaded shaft 105 and self-tapping end 130. In this embodiment, the head 110 clips onto the external surface of the outer sleeve 230. However, it is the internal groove 141 that allow the locking attachment to the driver.

With reference to FIGS. 20-26, a second embodiment is shown. In this embodiment, the fingers have been removed from the bone fastener 100 and in its place only the annular internal groove 141 is provided. On the outer sleeve 230, the fingers 240' have now been positioned so that the outer sleeve 230 has a plurality of fingers 240' that on attachment to the bone fastener 100 flex inwardly against the inner shaft 250 allowing the outer sleeve 230 to engage and have the fingers flex into the internal groove 141 of the bone fastener screw head 110. Again, as noted in this embodiment, in the distal engaged position, the outer sleeve bone fastener retaining distal end 240' is locked into the bone fastener screw head 110 as the inner shaft 250 provides the torque to insert the bone fastener 100 into the bone. Upon implantation of the bone fastener 100 into the bone, the inner shaft 250 can be moved to the proximal groove 252 to disengage the outer sleeve 230 from the bone fastener 100. This disengaged position allows the outer sleeve 230 to easily release itself from the attachment to the bone fastener 100.

With reference to FIGS. 27-33, a third embodiment of the invention is shown. In this embodiment, the bone fastener 100 is virtually the same as the bone fastener in the second embodiment. The bone fastener screw head 110 has an internal groove 141 that is annular and the outer sleeve 230 has a groove 241 for holding a split ring 245, the split ring 245 in a relaxed position is expanded outwardly radially but still held in the groove 241 of the outer sleeve 230. Upon insertion into the screw head 110, the split ring 245 compresses radially inwardly allowing it to flex past the lip of the screw head 110 and into the internal groove 141 where it springs outwardly locking or attaching the outer sleeve 230 to the bone fastener screw head 110. When the inner shaft 250 is in the distal engaged position, the bone fastener 100 can be securely threaded into the bone. Upon being fully inserted, the inner shaft 250 can be moved to a proximal position to disengage the bone fastener from the driver assembly 200.

As shown, each of these alternative embodiments provides a different way to create a locking feature of the driver with an outer sleeve and an inner shaft that moves proximally and distally to engage and disengage into a locking and unlocking feature.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:
1. A bone fastener driver system with a bone fastener retention feature, the system comprises:
 a bone fastener driver assembly having an outer sleeve, a handle and an inner shaft, the handle being fixed to said outer sleeve, wherein the handle has one or more ball detents configured to engage a pair of positioning grooves, the inner shaft with a distal end having a torque driving tip, the inner shaft fits through the handle and into the outer sleeve being coupled to the handle and axially movable relative to the handle and the outer sleeve from a proximal disengaged position to a distal engaged position, wherein the inner shaft has a proximal groove positioned to fix axially the proximal disengaged position when engaged with the one or more ball detents in the handle and a distal groove spaced distally relative to the proximal groove positioned to fix axially the distal engaged position when engaged with the one or more ball detents in the handle;
 one or more bone fasteners, each bone fastener having a bone fastener screw head with an internal groove or undercut, wherein the one or more bone fasteners each have a proximal end with a plurality of flexible fingers with a plurality of slots longitudinally extending between fingers formed above the internal groove or undercut configured to flex outwardly to attach onto an internal ring on the outer sleeve to attach the projections the driver to the bone fastener screw head; and
 wherein the outer sleeve has a bone fastener retaining distal end configured to lock into the internal groove or undercut of the bone fastener screw head when the inner shaft is axially moved from the proximal disengaged position to the distal engaged position to lock the bone fastener to the bone fastener driver assembly and upon a return movement of the inner shaft to the proximal disengaged position to unlock and release the bone fastener driver assembly from the bone fastener screw head.

2. The bone fastener driver system of claim 1 wherein the inner shaft when in the distal engaged position is configured to engage a torqueing aperture inside the bone fastener screw head as the outer shaft is locked into the internal groove or undercut of the bone fastener screw head and when the inner shaft is in the proximal disengaged position the outer shaft is unlocked from the internal groove or undercut and the driver can be disengaged from the bone fastener screw head.

3. The bone fastener driver system of claim 1 wherein the outer sleeve has a plurality of flexible fingers at the distal end of the outer sleeve and each of the one or more bone fasteners has the bone fastener screw head with an internal groove or undercut to receive the outer sleeve, each flexible finger having a projecting end configured to clip into the internal groove or undercut of the bone fastener screw head as the flexible fingers flex inwardly toward the inner shaft to engage the bone fastener screw head and spring lock the bone fastener screw head to lock and prevent movement of the bone fastener relative to the outer sleeve as the projecting ends enter the internal groove or undercut locking the bone fastener screw head to the driver when the inner shaft is positioned in the distal engaged position.

4. A bone fastener driver system with a bone fastener retention feature, the system comprises:

a bone fastener driver assembly having an outer sleeve, a handle and an inner shaft, the handle being fixed to said outer sleeve, wherein the handle has one or more ball detents configured to engage a pair of positioning grooves, the inner shaft with a distal end having a torque driving tip, the inner shaft fits through the handle and into the outer sleeve being coupled to the handle and axially movable relative to the handle and the outer sleeve from a proximal disengaged position to a distal engaged position, wherein the inner shaft has a proximal groove positioned to fix axially the proximal disengaged position when engaged with the one or more ball detents in the handle and a distal groove spaced distally relative to the proximal groove positioned to fix axially the distal engaged position when engaged with the one or more ball detents in the handle;

one or more bone fasteners, each bone fastener having a bone fastener screw head with an internal groove or undercut; and wherein the bone fastener driver assembly has the outer sleeve having a distal external groove configured to hold a split ring; and a split ring held in the distal external groove and protruding radially outwardly, the split ring being compressible and configured to compress on entry into the bone fastener screw head and upon aligning with the internal groove or undercut springs outwardly to attach the outer sleeve to the bone fastener and lock thereto when the inner shaft is moved to the distal engaged position.

5. The bone fastener driver system of claim 4 wherein the bone fastener when the inner shaft is moved to the proximal disengaged position, the split ring compresses as it flexes and is released from the bone fastener screw head.

* * * * *